United States Patent
Cunningham et al.

[11] Patent Number: 5,509,800
[45] Date of Patent: Apr. 23, 1996

[54] LIGHT-FILTER FOR DENTAL USE

[76] Inventors: Peter J Cunningham, 4 Howitt St., South Yarra Vic. 3141; Raymond A. Leggo, 7 Invernass Way, Nth. Balwyn Vic 3104, both of Australia

[21] Appl. No.: 293,691

[22] Filed: Aug. 19, 1994

[30] Foreign Application Priority Data

Aug. 20, 1993 [AU] Australia ................ PM0707

[51] Int. Cl.⁶ .......................... A61C 19/00; G02B 5/22
[52] U.S. Cl. .................. 433/29; 433/229; 359/889; 359/892
[58] Field of Search ................ 433/29, 30, 31, 433/229; 359/361, 889, 892, 885

[56] References Cited

U.S. PATENT DOCUMENTS

| | | | |
|---|---|---|---|
| 4,385,344 | 5/1983 | Gonser | 362/32 |
| 4,640,685 | 2/1987 | Croll | 433/141 |
| 4,652,085 | 3/1987 | Selling et al. | 359/892 |
| 4,655,712 | 4/1987 | Croll | 433/229 |
| 4,662,842 | 5/1987 | Croll | 433/229 |
| 4,737,104 | 4/1988 | Croll | 433/141 |
| 4,859,184 | 8/1989 | Hazard | 433/229 |
| 4,900,253 | 2/1990 | Landis | 433/30 |
| 4,952,143 | 8/1990 | Becker et al. | 433/32 |
| 5,288,231 | 2/1994 | Kuehn et al. | 433/29 |

*Primary Examiner*—Stephen Funk
*Attorney, Agent, or Firm*—Lorusso & Loud

[57] ABSTRACT

A light filter for dental use having a transparent planar member (12) which is colored so as to filter-out visible radiation in the range 400 nm to 520 nm, the range being that to which dental composite materials are sensitive, the filter being arranged to be fitted in front of a dental lamp by means of an attachment device (114) arranged to detachably secure the transparent planar member (12) to the dental lamp.

3 Claims, 1 Drawing Sheet

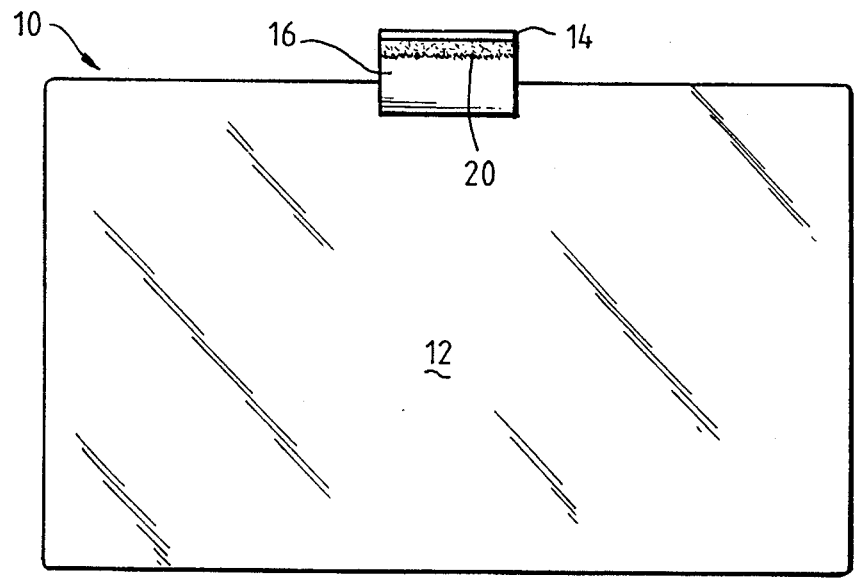
FIG. 1.
FIG. 2.
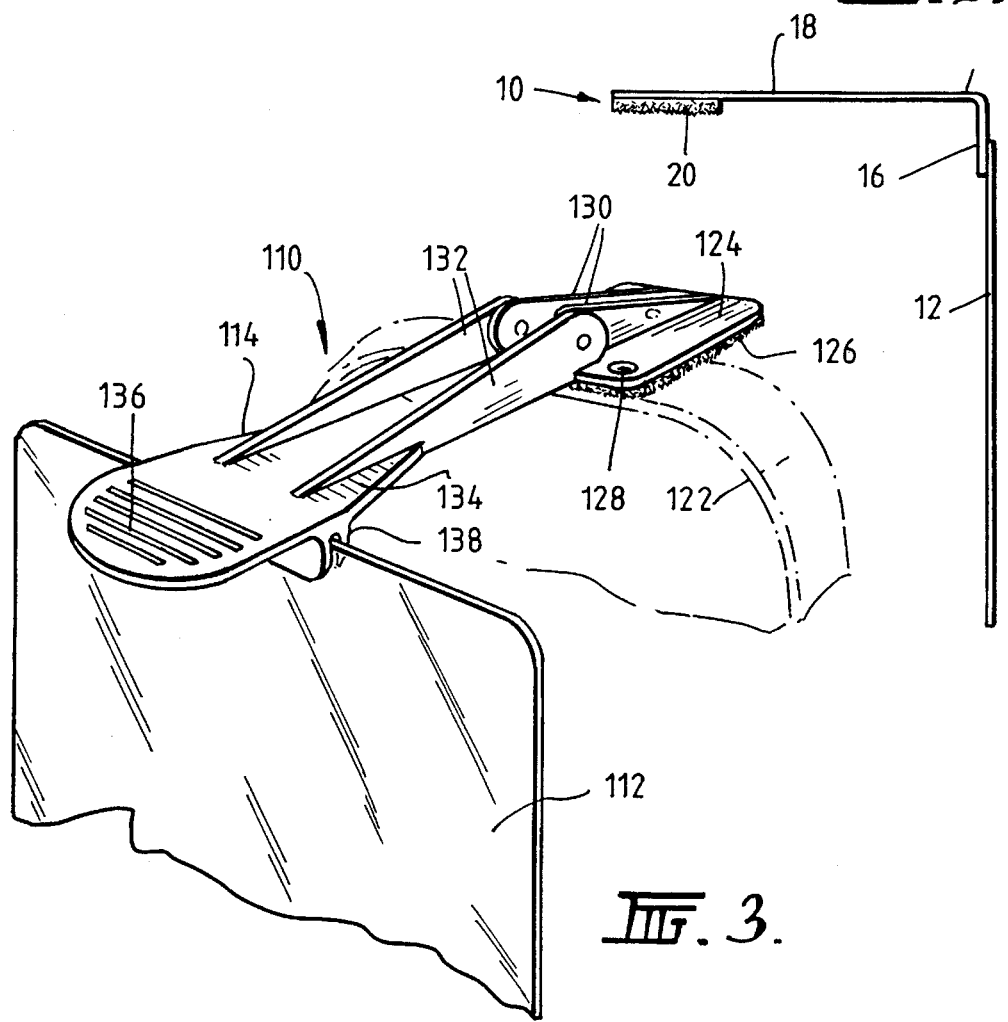
FIG. 3.

LIGHT-FILTER FOR DENTAL USE

FIELD OF THE INVENTION

The present invention relates to a light filter.

BACKGROUND OF THE INVENTION

Many tooth fillings nowadays use what are known as visible light-curable dental composite materials. The composite materials typically comprise a plastic material, a filler and a visible light sensitive compound which will cause the material to cure upon exposure to visible light.

Typically, a tooth is filled with the dental composite material in viscous paste form. The filling is then worked by the dentist to the desired configuration. Subsequently, the filling is cured by the dentist by means of a special light which emits visible light.

However, it has now been discovered that the dental composite material can cure prematurely because of radiation emitted by the dental lamp which generally illuminates patients' mouths during dental procedures. It has now been discovered that the premature curing is brought about because the dental composite material is sensitive to radiation at the lower end of the visible part of the electromagnetic spectrum, for example, in the range from 400 to 520 nm, preferably 450 to 470 nm, most preferably about 460 nm, and the dental lamp emits radiation in this wavelength range.

Dentists have been attempting to avoid this problem by turning off the dental lamp or turning it away while working with dental composite materials. However, this is unsatisfactory because the dentist then has insufficient light for correct working practices.

OBJECT OF THE INVENTION

The present invention provides a light filter which avoids the need to turn off the dental lamp and reduces the degree of premature curing of the dental composite material.

SUMMARY OF THE INVENTION

In accordance with one aspect of the present invention, there is provided a light filter for dental use comprising a transparent planar member which is colored so as to filter-out visible radiation in the range of 400 nm to 520 nm, said range being that to which dental composite materials are sensitive, said filter being arranged to be fitted in front of a dental lamp by means of an attachment device arranged to detachably secure the transparent planar member to the dental lamp.

DESCRIPTION OF THE DRAWING

The present invention will now be described, by way of example, with reference to the accompanying drawings, in which:

FIG. 1 is a front elevation of a light filter in accordance with the present invention;

FIG. 2 is a side elevation of the light filter of FIG. 1; and

FIG. 3 is a front perspective view of a light filter in accordance with the present invention as attached to a dental lamp.

DESCRIPTION OF THE PREFERRED EMBODIMENT

In FIGS. 1 and 2 of the drawings there is shown a light filter 10 comprising a transparent planar member 12 which is generally, as shown, relatively thin and of rectangular shape when viewed from the front. In the embodiment shown, the planar member 12 is flat, but it could be of arcuate configuration. Also, the rectangular shape could be replaced by a circular or other suitable shape. The transparent planar member 12 can be of any suitable dimensions.

The transparent planar member 12 can be formed of any suitable material such as a sheet of plastic material or a layer of gel laminated between two flat sheets. In any event, the transparent member 12 has to be colored so that it will filter out visible light having wavelengths to which dental composite materials are sensitive, for example, in the range from 400 nm to 520 nm, preferably 450 nm to 470 nm, most preferably about 460 nm.

Attached to the transparent member 12 by any convenient means is an attachment device, such as an L-shaped bracket 14. As can be seen, the L-shaped bracket 14 is attached to the member 12 along at least part of one edge of the member 12 by a relatively short arm 16.

Further, the bracket 14 has a relatively long arm 18 which extends away from the member 12 at about 90°. At the end thereof remote from the member 12, the arm 18 has provided at one side thereof an attachment means 20.

The attachment means 20 can take many forms but it has to be such that the light filter 10 can be readily attached to and detached from a dental lamp. Preferably, the attachment means 20 is in the form of one half of a Velcro™ fastener with the other half being securely attached to the dental lamp.

In use, when a dentist wants to work with a dental composite material he first secures the light filter 10 to the dental lamp by the attachment means 20 so that the transparent member 12 is interposed between the dental lamp and the patient's mouth. In this way, visible light to which the dental composite material is sensitive is filtered out and premature curing of the dental composite material is reduced. When the dentist has finished working with the dental composite material he can simply remove the light filter 10 from the dental lamp until the light filter 10 is required again.

To refer now to FIG. 3 there is shown a second embodiment of the attachment device. A light filter generally designated as 110 comprises a transparent planar member 112 which is the same as the transparent planar member 12 of FIGS. 1 and 2. Light filter 110 also comprises a bracket 114 used to attach the transparent planar member 112 to a dental lamp 122.

The bracket 114 has an attachment member 124 which is secured to the lamp 122 by means of Velcro™ 126 or other like attachment means. For example, screw holes 128 may be provided in case of screw attachment being required. An alternative would be gluing. On the upper surface of the attachment member 124 are two ribs 130 which form a hinged connection with connecting members 132 of arm 134. At its outer end 136, arm 134 has a tab-like member which is easily gripped or contacted by the finger of the dentist to move the arm 134. Underneath arm 134 is a channel member 138 into which the transparent planar member 112 can be securely but releasably placed.

As can be seen, the attachment member 124 can be either releasably or securely attached to the dental lamp 122. By virtue of the hinged connection at the junction of the ribs 130 and the connecting members 132, the arm 134 of the bracket 114 can be moved to be in front of, or above, the lamp. In this way, the transparent planar member 112 will be in front of the lamp when required when the dentist is working on the composite material in a patient's mouth, or above the lamp so that full light is available at other times.

We claim:

1. A light filter for dental use comprising:

a transparent planar member colored so as to filter-out visible radiation in the range of 400 nm to 520 nm, said range being that to which dental composite materials are sensitive; and an attachment device configured to detachably secure said transparent planar member to a dental lamp such that said planar member is placed in front of the dental lamp, said attachment device including, an attachment member for attachment to the dental lamp, said attachment member having at least one longitudinally extending rib extending upwardly therefrom, and an arm having an outer end for receiving said planar member, said arm hingedly coupled to said at least one rib.

2. A light filter for dental use as claimed in claim 1, wherein said outer end has a tab-like projection which is finger engageable by a user.

3. A light filter for dental use as claimed in claim 1, wherein said arm has extending therefrom a channel-like member which is adapted to securely but releasably receive said transparent planar member.

* * * * *